United States Patent [19]
McNeal et al.

[11] Patent Number: 5,294,311
[45] Date of Patent: * Mar. 15, 1994

[54] SALT BRIDGE FOR ANALYTICAL CHEMISTRY SYSTEM

[75] Inventors: Jack D. McNeal, Long Beach; Delbert D. Jackson, Placentia; Theodore R. Nichols, Fullerton, all of Calif.

[73] Assignee: Beckman Instruments, Inc., Fullerton, Calif.

[*] Notice: The portion of the term of this patent subsequent to Jul. 14, 2009 has been disclaimed.

[21] Appl. No.: 862,185

[22] Filed: Apr. 2, 1992

Related U.S. Application Data

[63] Continuation of Ser. No. 322,811, Mar. 13, 1989, Pat. No. 5,130,010.

[51] Int. Cl.$^5$ ............................................. G01N 27/28
[52] U.S. Cl. ............................. 204/153.1; 204/411; 204/435
[58] Field of Search .................. 204/411, 435, 153.1

[56] References Cited

U.S. PATENT DOCUMENTS

| | | | |
|---|---|---|---|
| 3,264,205 | 8/1966 | Leonard | 204/195 |
| 3,501,392 | 3/1970 | Ayers | 204/435 |
| 4,003,705 | 1/1977 | Buzza et al. | 23/230 |
| 4,170,523 | 10/1979 | Buzza et al. | 204/11 |
| 4,255,244 | 3/1981 | Matsuyama et al. | 204/195 |
| 4,413,628 | 11/1983 | Tamulis | 128/635 |
| 4,490,234 | 12/1984 | Buzza | 204/409 |
| 4,889,611 | 12/1989 | Blough, Jr. | 204/411 |
| 5,130,010 | 7/1992 | McNeal et al. | 204/411 |

FOREIGN PATENT DOCUMENTS

| | | |
|---|---|---|
| 0094677 | 11/1983 | European Pat. Off. . |
| 0101237 | 2/1984 | European Pat. Off. . |
| 0122420 | 10/1984 | European Pat. Off. . |

OTHER PUBLICATIONS

*System E4A Operating Manual,* Beckman Instruments, Inc., Clinical Instruments Division, Brea, Calif., Section Three, Principles of Operation, pp. 3-1 through 3-8, 1982.

Primary Examiner—John Niebling
Assistant Examiner—Arun S. Phasge
Attorney, Agent, or Firm—William H. May; Gary T. Hampson; Sarah B. Adriano

[57] ABSTRACT

A salt bridge for a flow cell which includes a porous bridge element between fluid flow in the flow cell and in an internal reference fluid flow. The bridge element is surrounded by a body with a bore into which different tubes are located about the porous element. A cylindrical anchoring tube adjacent one end of the body is screw threaded into an aperture in the wall of the flow cell so that self-alignment of the salt bridge in the flow cell is effected. The salt bridge provides a conductivity path between the two flow paths without introducing another potential.

13 Claims, 1 Drawing Sheet

SALT BRIDGE FOR ANALYTICAL CHEMISTRY SYSTEM

This is a continuation, of the application Ser. No. 07/322,811, filed Mar. 13, 1989, now U.S. Pat. No. 5,130,010.

RELATED APPLICATIONS

This invention relates to the inventions and disclosures which are the subject of application Ser. Nos.:
07/322,814 filed Mar. 13, 1989 now abandoned.
07/322,802 filed Mar. 13, 1989 now U.S. Pat. No. 5,182,083.
07/322,810 filed Mar. 13, 1989 now U.S. Pat. No. 4,915,713.
07/322,811 filed Mar. 13, 1989, now U.S. Pat. No. 5,130,010, issued Jul. 14, 1992.
07/322,812 filed Mar. 13, 1989 now abandoned.
07/322,813 filed Mar. 13, 1989 now U.S. Pat. No. 5,132,223.
07/322,807 filed Mar. 13, 1989 now U.S. Pat. No. 5,130,095.

All these applications are filed contemporaneously with the present application and the contents of them are incorporated by reference herein.

BACKGROUND

This invention relates to the field of electrodes for automatic analytical chemical instruments. More particularly, the invention is concerned with a salt bridge in flow cells of analytical instruments.

Flow cell analyzers operate with a combined mixture of diluent and fluid sample flow past various electrodes for the determination of electrolytes in the fluid sample. Usually four electrolytes, namely, sodium, potassium, chloride and $CO_2$ are determined in the flow cell. It is often desirable to connect different flow paths together without introducing new potential to the electrodes. The salt bridge provides a non-flow or very low flow path between these different flow paths and in effect a conductivity path.

In the prior art, salt bridges are relatively permanently located in a flow cell, and have drawbacks in that they are difficult to align and assemble relative to the flow cell and different flow streams. The alignment of the salt bridge is particularly critical. It is thus difficult to set the salt bridge effectively and accurately in the flow cell. Additionally, when maintenance is necessary and the salt bridge needs to be removed from the flow cell, it is necessary to disassemble the entire flow cell. Difficulties also arise in the creation of air bubbles in adjacency with elements of the salt bridge electrode so that electrolyte measurements are inaccurate.

The present invention seeks to overcome these drawbacks and to provide a salt bridge element which is relatively simple to locate in a flow cell in self-alignment.

SUMMARY

The present invention provides a salt bridge for a flow cell of a chemical analyzer, where the device includes a salt bridge in a self-aligning body which overcomes the problems in the prior art.

According to the invention, a salt bridge for a flow cell in a chemical analyzer comprises a porous bridge element for location in an aperture having access to the fluid paths in a flow cell. The porous bridge element has one surface portion exposed to the fluid flow path of a flow cell and a different portion exposed to the flow of a reference fluid. The two portions are spaced and form between them a salt bridge, namely, a conductivity path. There is means for removably securing the porous element between the fluid flows and in alignment in the aperture.

In a preferred form of the invention, the securing means includes a body surrounding the bridge element. There is also a cylindrical anchoring tube threaded on the outside, the threads being for screw engagement to the aperture in the flow cell.

Also in a preferred form of the invention, the bridge element is surrounded by a selected arrangement of cylindrical sleeves. There is preferably a lead-in cylindrical sleeve provided to the body for internal reference fluid to be positively directed to the one exposed portion of the bridge element. There is preferably a low resistivity and slow diffusion rate between the two exposed portions of the bridge element.

The invention is further described in the following detailed description with reference to the accompanying drawings.

DRAWINGS

FIG. 1 a diagrammatic external side view of a salt bridge.

FIG. 2 a diagrammatic cross-sectional enlarged view of the salt bridge located in an aperture associated with the flow cell and showing the internal reference fluid inlet and exit.

DESCRIPTION

Figure 1:
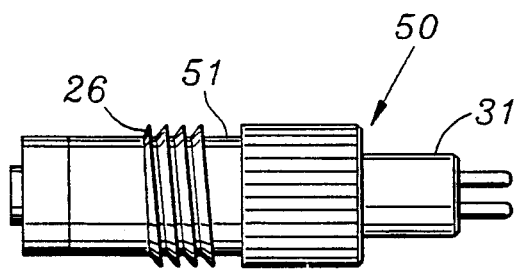
Figure 2:
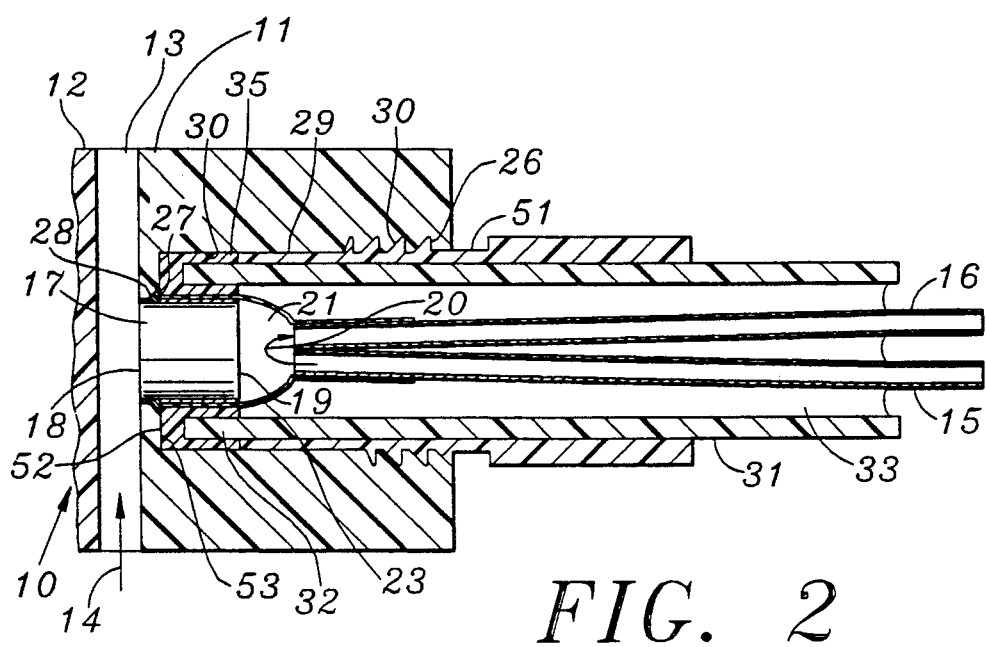
Figure 3:
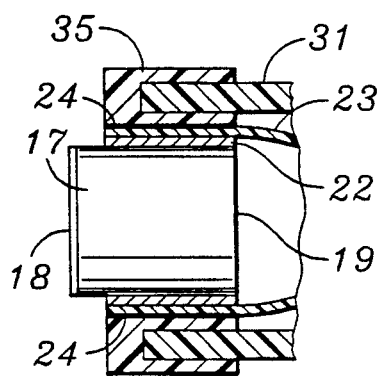
FIG. 3 is an enlarged partial view of the salt bridge element.

In an automatic chemistry analyzer there is a flow cell 10 which is diagrammatically illustrated, in part. The flow cell lo is an element of an analyzer where different electrolytes, such as sodium, potassium, chloride and $CO_2$ are measured by the flow cell 10. The cell 10 is formed between two clamped plates 11 and 12. A flow path 13 for sample fluid and diluent to travel as indicated by arrow 14 is formed between the plates 11 and 12.

An internal reference fluid enters the salt bridge 50 through an inlet tube 15 and exits through an outlet tube 16 The internal reference fluid is supplied directly or indirectly from a container in the analyzer. After passage from tube 16 the fluid is drained directly or indirectly to a suitable reservoir which may be a waste reservoir. If the fluid is indirectly fed to and from the electrode 50 there may be other electrodes to or from which the internal reference fluid is directed.

The salt bridge 50 includes a bridge element 17 with the first exposed portion 18 adjacent the fluid flow 14 in the flow cell 10. A second exposed portion 19 is adjacent to fluid flow 20 through the internal reference tubes 15 and 16. A chamber 21 is formed between the inlet tube 15 for the internal reference fluid and exit tube 16 for the internal reference fluid.

The bridge element 17 is constituted by a porous material, and is selectively a glass rod covered with a ceramic coating, a porous ceramic rod or a plastic porous fiber material The material can be silk thread, ceramic tubing, fibrous porous plastic or similar porous material. There is a slow diffusion rate between the one surface exposed portion 18 and the other surface exposed portion 19. The resistivity is about 200 Kohms.

About the bridge element 17 there is provided a ceramic coating 22 and about that ceramic coating 22 there is formed a shrink tube 23. An epoxy material 24 is formed about the shrink tube 23 and is used to bond the assembly of shrink tube 23 and bridge element 17 into the salt bridge tip 35.

The outer surface of the epoxy 24 is surrounded by a cylindrical body which form the salt bridge tip body 35. A bore in the body 35 accommodates the bridge element 17 and surrounding tubes. The body 35 includes a circular outer periphery and a shoulder section 27 about which an O-ring 28 can be located in adjacency to the aperture 29 in the wall 11 of the flow cell 10. The wall 11, which is the back wall of the flow cell 10, acts as the anchor for the salt bridge 50. The O-ring 28 facilitates positive and accurate location of the salt bridge 50 with the wall 11 and prevents leakage. The aperture 29 includes a tapered circular portion 30 against which the O-ring 28 is located. The location of the body 35 in the aperture 29 is positively established as a cylindrical anchoring tube 51 with a threaded outer surface 26 engaging the internal threaded surface 30 in the aperture 29 to the wall 11 of the flow cell 10. The cylindrical anchoring tube 51 is adjacent the end of the body 35 remote from the flow cell path 13. The tube 51 can slide longitudinally to effect anchorage with the flow cell wall 11.

Extending in a leading direction from the bridge tip 35 is a lead-in cylindrical tube 31 which is affixed in a circumferential slot 32, within the trailing end of the tip 35. Within the lead portion 31 there is housed a setting material 33 through which the inlet and outlet tubes 15 and 16 pass and are cemented. The cylindrical anchoring tube 51 extends about the lead-in cylindrical tube 31 for the sliding action. The shrink tube 23 extends beyond the bridge element 17 and engages the inlet tube 15 and outlet tube 16 in a sealing relationship.

The component design is one where the bridge element 17 acts as a salt bridge, and is relatively easy to insert and remove from the flow cell 10. The salt bridge is self-aligning and non-critical as the body 25 of the salt bridge 50 and lead-in portion 31 screw thread into connection with anchoring wall 11 associated with the flow cell 10. This is effected by means for the tube 51 which threadingly, through threads 26 and 30, engages aperture 29. As the tube 51 is tightened in the aperture the leading end 52 of the tip 35 is forced into tight engagement with the corresponding circumferential ring face 53 about aperture 29. The shoulder section 27 engages O-ring 28.

The positive location of internal reference fluid inflow 15 and exit tube 16 avoids the trapping of air or gas bubbles in the chamber 21 adjacent to portion 19 of the salt bridge. The flow through the chamber 21 is relatively laminar and the chamber 21 surfaces are of a nature inhibiting entrapment of air or gas. Air bubbles are also avoided at the portion 18 by the characteristics of the bridge element 17 and surrounding tubes.

Figure 4:
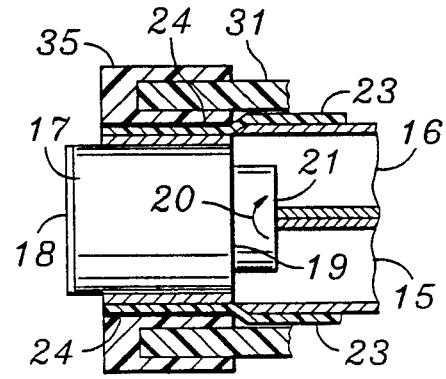
FIG. 4 is a diagrammatic view of a different embodiment of the salt bridge in relation with inlet and exit tubes for the reference fluid.

In FIG. 4, there is shown an embodiment where the inflow tube 15 and exit tube 16 are jammed up against the portion 19 of the element 17. The ends of tubes 15 and 16 are half cut away about semi-circular sections so that between the semi-circular cut out sections from each of tubes 15 and 16 there is formed a chamber 21 for fluid flow 20.

Many other examples of the invention exist, each different from the other in matters of detail only. For instance, different bonding materials can be used about the porous bridging element to effect the positive location in the cylindrical body. Also, different fluids can enter the chamber about the one exposed portion of the porous bridging element. The scope of the invention is to be determined solely by the following claims.

We claim:

1. A salt bridge for a flow cell of a chemistry analyzer, the salt bridge being constituted by an integral arrangement comprising a porous bridge element for location in an aperture in a flow cell, the porous bridge element having a first portion for exposure to fluid flow through a path in the flow cell and a second portion for exposure to flow of a reference fluid through internal reference tubes, the second portion being adjacent to fluid flow through the internal reference tubes, the two portions being spaced to form between them a salt bridge, means for reference fluid to flow towards and from the second portion of the element, means for locating the porous bridge element between the fluid flow in the flow cell and the flow of the reference fluid, the locating means being for securing the porous bridge element in alignment in the aperture such that the first portion is exposed to flow through the path and the second portion is exposed to flow of the reference fluid, and the means for locating the bridge including an anchoring rube for removable location with the flow cell such that the removal of the tube removes the bridge from the aperture in the flow cell, and the means for reference fluid flow towards and from the element.

2. A salt bridge as claimed in claim 1 wherein the anchoring tube includes an outer threaded surface, the outer threaded surface being for engagement with threads in the aperture of the flow cell.

3. A salt bridge as claimed in claim 1 wherein between the porous bridge element and the sleeve body there are further sleeve elements, the further sleeve elements being selectively a ceramic tube surrounded by a shrink tube and an epoxy bond, the sleeve body having a bore sufficiently large for accommodating the tubes.

4. A salt bridge as claimed in claim 1 including a lead-in cylindrical tube for location remotely of the flow cell path, the lead-in cylindrical tube having separate means for the reference fluid to enter and to exit from the second portion of the bridge element.

5. A salt bridge as claimed in claim 4 wherein between the inlet and exit for the reference fluid there is a chamber adjacent the portion of the bridge element exposed to flow of the reference fluid.

6. A salt bridge as claimed in claim 5 wherein the inlet and exit includes tubes for the reference fluid, the tubes being anchored in the lead-in cylinder.

7. A salt bridge as claimed in claim 1 including a circular outer periphery to the body, the circular outer periphery including a shoulder for locating an O-ring adjacent to a wall of the flow cell.

8. A salt bridge as claimed in claim 1 wherein the porous bridge element is selectively a ceramic-coated glass rod, silk or cotton thread, ceramic tubing, fibrous plastic or porous plastic.

9. A salt bridge as claimed in claim 1 wherein the porous bridge element provides for a relatively slow diffusion rate between the first portion and the second portion.

10. A method of aligning a salt bridge for a flow cell of a chemistry analyzer in an aperture in a flow cell, the salt bridge being constituted in an integral arrangement comprising the steps of:
 a) anchoring a locating body in an aperture for the flow cell,
 b) exposing a first portion of a porous bridge element of the cell to fluid flow through a path in the flow cell,
 c) exposing a second portion of the element to flow of a reference fluid, the first portion and the second portion being spaced to form between them the salt bridge, and
 d) locating the porous element in alignment in the aperture so that the first portion is exposed to the flow in the path and the second portion is exposed to flow of the reference fluid, and the bridge being selectively removable from the aperture in the flow cell, together with the locating tube and reference fluid feed.

11. A method as claimed in claim 10 wherein the locating body is a cylindrical anchoring tube with an outer threaded surface, and including causing the outer threaded surface to engage with threads in the aperture to the flow cell and be located in alignment in the aperture, and thereby urge the bridge element into alignment in the aperture.

12. A method as claimed in claim 11 including housing the porous bridge element in a sleeve body, and locating further sleeve elements between the sleeve body and the bridge element.

13. A method as claimed in claim 12 including urging a circular outer periphery to the body, to engage an O-ring seal adjacent a wall of the flow cell.

* * * * *